United States Patent
Watkins

(10) Patent No.: US 6,646,014 B2
(45) Date of Patent: Nov. 11, 2003

(54) ORGANIC COMPOUNDS

(75) Inventor: Max Watkins, Odiham (GB)

(73) Assignee: Vita (Europe) Limited, Hants (GB)

( * ) Notice: Subject to any disclaimer, the term of this patent is extended or adjusted under 35 U.S.C. 154(b) by 0 days.

(21) Appl. No.: 09/765,601

(22) Filed: Jan. 22, 2001

(65) Prior Publication Data

US 2001/0014346 A1 Aug. 16, 2001

Related U.S. Application Data

(63) Continuation of application No. 08/991,779, filed as application No. PCT/EP97/03078 on Jun. 12, 1997, now abandoned.

(30) Foreign Application Priority Data

Jun. 13, 1996 (GB) ............................................. 9612403

(51) Int. Cl.$^7$ ........................ A01N 31/08; A01N 25/04; A01N 25/34
(52) U.S. Cl. ........................ 514/731; 514/919; 514/944; 514/953; 514/964; 424/405; 424/408; 424/409; 424/456; 424/457; 424/468; 424/484; 424/485; 424/486; 424/492
(58) Field of Search ................................. 514/731, 944, 514/964, 919, 953; 424/409, 456, 457, 492, 405, 408, 468, 484, 485, 486

(56) References Cited

U.S. PATENT DOCUMENTS

| 4,316,887 A | * | 2/1982 | Kamishita et al. | 514/692 |
| 5,073,366 A | * | 12/1991 | Beck | 424/720 |
| 5,631,024 A | | 5/1997 | Kevan et al. | 424/486 |
| 5,964,905 A | * | 10/1999 | Camp et al. | 44/275 |

FOREIGN PATENT DOCUMENTS

| JP | 63-260956 | | 10/1988 |
| RU | 2038777 C1 | | 7/1995 |
| RU | 2045176 C1 | | 10/1995 |
| RU | 2058731 C1 | | 4/1996 |
| SU | 1674760 A1 | | 9/1991 |
| SU | 1676554 | * | 9/1991 |

OTHER PUBLICATIONS

Chemical Abstracts 122:284566z (1995).*
Chemical Abstracts 98:193274x (1983).*
Chemical Abstracts 110:71152b (1989).*
Chemical Abstracts 121:101800h (1994).*
Nelson et al., "Formic acid application methods for the control of honey bee tracheal mites," Bee Science, Vo. 3(3), Jun. 1994, pp. 128–134.*
Derwent Abstract, accession No. 1992–19806; abstracting SU 1676554, Sep. 1991.*
Nelson, D. et al., "Effectiveness and residue levels of 3 methods of menthol application to honey bee colonies for the control of tracheal mites," Apidologie, vol. 24, 1993, pp. 549–556.*

* cited by examiner

Primary Examiner—John Pak
(74) Attorney, Agent, or Firm—Foley & Lardner

(57) ABSTRACT

The present invention concerns a method for the control of various diseases in bee-hives by applying to the bee-hives an effective amount of an essential oil in a slow-release formulation whereby the term oils embraces but is not limited to oils extractable from plant or the essential component thereof such as monoterpenes like menthol, geraniol, thymol, myrcene, citral, limonene, carene, camphor, eugenol, or cineol (eucalyptol); natural oils like lemon oil, eucalyptus oil, or neem oil; or organic acids like formic acid, acetic acid or oxalic acid. Most preferred are monoterpenes like thymol or menthol. Most preferred is thymol.

4 Claims, No Drawings

ORGANIC COMPOUNDS

This application is a continuation of 08/991,779 filed Dec. 16, 1997 now abandoned, which is a 371 of PCT/EP97/03078, filed on Jun. 12, 1997.

The present invention concerns a method for the control of acarid, lepidopteran, fungal, and bacterial infestations of honeybee colonies, and infestation controlling compositions suitable for such purpose.

Varroasis is an infestation of European honeybee colonies (*Apis mellifera*) with the ectoparasitic mites belonging to the order of acaricides (*Varroa jacobsoni*).

The Varroa mite originated in Asia and from there has spread to virtually all countries where beekeeping with *A. mellifera* is practised.

In addition, other acarine infestations such as those of *Acarapis woodii* (Tracheal mite) and *Tropilaelaps clareae;* lepidopteran infestations such as those of the Greater and Lesser wax moths, *Galleria mellonella* and *Achroia grisella* respectively; dipteran infestation such as that of *Braula caeca;* fungal infection such as that of Chalk Brood, *Ascosphaera apis* and bacterial infections such as those of the American and the European Foulbroods, Bacillus larvae and *Melissococcus pluton* respectively, can cause significant damage to honeybee colony health.

The Varroa mites feed of the haemolymph of the developing bees and adults alike and can result in stunted growth of bees, infection and death of bee colonies. Indeed varroa infestation is the most serious threat to beekeeping worldwide today.

Various treatments are available for the control of this disease. However, in certain regions of Southern Europe, the Varroa mite has developed a resistance to the active ingredient of some of these various treatments, notably to products based on the pyrethroids flumethrin, fluvalinate and acrinathrin, but also to coumaphos, amitraz, malathion, cymiazole hydrochloride, chlorfenvinphos, bromopropylate, fenpyroximate, and related molecules.

There is a need, therefore, for a new treatment for varroa and other infestations.

SUMMARY OF THE INVENTION

It has now been found that the various diseases in beehives can be efficiently controlled by applying to the beehives an effective amount of an essential oil or an organic acid in a slow-release formulation.

The present invention provides for a method for controlling acarid, lepidopteran, fungal and bacterial pest infestations in colonies of honeybees, which comprises the application of an effective amount of an essential oil or an organic acid in a slow-release formulation to the locus of honeybee colonies.

The invention furthermore provides a slow-release gel formulation for the control of acarid, lepidopteran, fungal and bacterial infestations in colonies of honeybees, comprising an effective amount of an essential oil or organic acid in order to administer effective levels of said oil or acid.

DETAILED DESCRIPTION OF THE INVENTION

For the purpose of this invention, the locus of colonies of honeybees is usually understood, but not limited, to beehives, or similar containers where colonies of bees build their breeding places and store food reserves, such as honeycombs. Preferably, the locus of honeybee colonies as referred to herein in a beehive.

As used herein, a "pest" is any organism, which may be an acarid, lepidopteran, fungal and/or bacterial organism, which infests honeybee colonies.

According to the present invention, essential oils and/or organic acids are applied in slow-release formulations in order to combat infestation of honeybee colonies by pests. Preferably, the method of the invention comprises applying an essential oil.

An essential oil is understood to comprise oils extractable from plants or the essential component thereof, which may be in solid form under certain conditions. Examples of essential oils are monoterpenes, such as menthol, geraniol, thymol, myrcene, citral, limonene, carene, camphor, eugenol, or cineol (eucalyptol); and natural oils such as lemon oil, eucalyptus oil, or neem oil. Examples of organic acids include acids such as formic acid, acetic acid or oxalic acid. Preferred essential oils for use in the present invention comprise monoterpenes such as thymol or menthol. Most preferred is thymol.

In a preferred embodiment, methods according to the present invention comprise the application of only a single essential oil or organic acid. Alternatively, however, mixtures of two or more essential oils and organic acids may be used. Optionally, the method may entail the application of a mixture of essential oils and organic acids.

As used herein, a "slow-release formulation" is meant to signify a formulation developed specifically to behave in a certain manner under defined conditions, characterised by a more regulated administration of active material over a given time-frame in comparison to raw active material. In particular, such formulations in connection with volatile essential oils, are capable of maintaining a constant vapour concentration of the essential oil in the atmosphere of an enclosed volume of a bee-habitat, i.e. a bee-hive. The proposed slow-release formulation is thus capable of releasing a regulated dose at a constant rate, preferably releasing a defined quantity of essential oil into a bee-hive over a chosen period of time, such as the reproductive cycle of the targetted pest. Preferably controlled elivery is achieved over a period of 4–6 weeks, this period constituting at least one varroa mite reproductive cycle.

The active ingredient (essential oil or organic acid) is transported from the formulation via the vapour phase onto the target pest. In a preferred aspect of the invention, the essential oil evaporates or sublimates from the formulation in a regulated concentration into the atmosphere of the bee-environment (e.g. the beehive) and maintains the pre-selected concentration for at least a 4 to 6 week treatment period. Though the atmosphere in the bee environment is not hermetically sealed, the various pests in said environment can be effectively controlled by the release of the essential oil form the slow-release formulation. This also applies to the pests affecting the bee larvae in the brood chambers, which can be effectively protected by this method.

The method of control of varroa infestations according to the present invention is both effective against pyrethroid resistant and susceptible Varroa mite strains in bee-hives. In a preferred embodiment of the invention, effective control of infestations, particularly varroa infestations, may be acieved such that the infestation is reduced to a level of 20% or less of a starting infestation level within at least one pest reproductive cycle. The "starting infestation level" is the infestation level before treatment is initiated. Preferably, the reduction in infestation levels to 20% is achieved within one pest life cycle, for example the 4–6 weeks of a varroa life cycle.

From the literature, the use of thymol in non-slow release formulations for attempting the control of Varroa infestations is known. Moreover, the use of thymol as a control agent against the bee tracheael mite *Acarapis woodii* had been suggested. However, the level of control achieved by hive treatment with the raw material is low, and at best variable. With raw material the natural rate of evaporation from the crystal, powder or liquid forms is largely dependent on ambient temperature, with the result that the dose administered to a beehive cannot be adequately regulated in the raw product form. For example, varroa treatment of bee colonies with thymol either requires multiple applications or high application doses, both of which methods cause honeybees to reject the hive. High doses are also toxic to the sensitive bee larvae.

The above disadvantages can be avoided by the method of the present invention. The new method is not only effective against varroa, but also controls all the other honeybee disease organisms aforementioned.

Examples of a slow-release formulation according to the present invention are gel formulations, either stand-alone or on bee-acceptable supports; impregnated materials; or polymer matrixes incorporating the above-mentioned essential oils or organic acids. Treatment of the infested bee colonies is preferably done in form of gel, or a gel strip, gel pellets, gel tablets, or in a dispenser tray filled with any of the above forms, or any other type of slow-release dispersing system.

A slow-release matrix formulation may be presented in any type of dispensing system, for example a shallow plastic tray dispenser with a hermetically sealing lid like a plastic or aluminium seal lid. The slow-release formulations used in the method according to the present invention are prepared according to methods known to the person of ordinary skill in the art. However, the slow-release formulations according to the present invention are preferably matrix-forming gels, which comprise the essential oil or organic acid in pure form or as a liquid formulation and a gel-forming amount of a thickener component and a bee-acceptable carrier material. This formulation type is suitable both for solid or liquid essential oils.

Polymers of acrylic acid are in particular suitable as thickener components. Commercial products available for this purpose are: carboxypolymethylenes, carboxyvinylpolymers, or carbomers like a CARBOPOL® (B. F. Goodrich Corp., Cleveland, Ohio). Other suitable thickener components are for instance carboxymethylcelluloses, polyvinyl acetate alcohols like a MOWIOL® (HOECHST AG, Frankfurt, Germany), long chain ammonium salts like BENTONE® (RHEOX GmbH, Leverkusen, Germany), hydrophilic polysaccharides like RHODOPOL® (RHONE POULENC, Paris) or KELZAN® (KELCO COMP. San Diego), or cellulose derivatives like TYLOSE (HOECHST AG, Frankfurt, Germany).

In a preferred embodiment, the slow-release formulations according to the present invention comprise the active substance (essential oil or organic acid), the thickener agent with a cross-linking agent, and water, but do not require any additional detergent to be present.

Typical concentrations of the thickener in the slow-release formulation are from 0.01 to 1.5% of the total weight of the composition, preferably 0.1 to 1.0%, e.g. 0.3%, 0.4% or 0.5%. The actual concentration is however easily determinable by the worker of ordinary skill in the art, according to the desired concentration of the essential oil in the bee-environment and the size of said environment.

The concentration of the essential oil in the overall composition is not critical, but may be between 5 and 50% of the total weight of the composition. Preferably, the concentration is between 10% and 40%, e.g. 20%, 25% or 30%.

The mixture ratio of the essential oil to the thickener depends mainly on the amount of thickener required to transform the essential oil or organic acid and carrier mixture into a gel. In the given ranges of components, it is between 3:1 and 5000:1, preferably between 30:1 and 90:1, e.g. 40:1, 50:1, 60:1, or 70:1.

In a typical preparation of the slow-release formulation the liquid or solid essential oil is added to a dispersion of the thickener like polyacrylic acid (e.g. CARBOPOL® EZ1) in water, and then the mixture is cross-linked by adding a suitable amount of a tertiary or secondary amine, for example 0.01% to 2% of triethanolamine.

The cross-linking of the polyacrylic acid with an multifunctional amine gives the obtained gel a matrix-like structure.

The obtained slow-release-formulation provides for releasing an effective amount of essential acid or organic acid over a defined period of treatment. By "effective amount" it is intended to denote a sufficient amount of essential oil or organic acid to achieve at least 80% infestation control of the parasite/pathogen without effecting significant mortality of the honeybee colony. The actual required and desirable concentration in the beehive can easily be determined by routine experimentation.

The new formulations so prepared provide the following advantageous properties:

1) The formulation releases a regulated dose of the active substance (essential oil or organic acid) into the beehive over a defined period of time and temperature range of 10–40 degrees Centigrade.
2) The formulation is highly effective in the control of pyrethroid-resistant as well as susceptible *Varroa jacobsoni* mites, parasitic on honeybees.
3) The formulation is also having efficacy against tracheal mite, *A. woodii;* the Greater and Lesser wax moth, *Galleria mellonella* and *Achroia grisella* respectively; the dipteran pest *Braula caeca;* fungal infections such as Chalk Brood, *Ascosphaera apis,* and bacterial infections such as those of the American and the European Foulbroods, Bacillus larvae and *Melissococcus pluton,* respectively.

The method of the present invention is preferably and ideally applied to bee populations or the bee environment in early spring or late summer, i.e. before or after the main honey flows but may not be restricted to these periods.

The slow-release formulation may be introduced to the interior of the beehive and left in place for a defined period of time, treatment duration being not shorter than 4 weeks and not longer than 6 weeks, at which time the formulation is to be removed from the hive.

Depending on the climatic region, it may be necessary to perform a second such treatment later in the year due to differences in reinfestation pressure.

The invention is further described below, for the purpose of illustrration only, in the following examples.

EXAMPLE 1

Preparation of a Thymol Slow-Release Formulation 0.38 parts of CARBOPOL® EZ1 are slowly added to 73.86 parts of water with stirring. 25 parts of thymol are finely crushed and added to the stirred mixture. To the obtained dispersion, 0.76 parts of a 50% aqueous solution of triethanolamine is added for cross-linking purposes, forming a gel.

The gel mixture is divided into 50 g portions and placed on shallow plastic tray dispensers. The surface of the tray is hermetically sealed with an aluminium or plastic foil lid. Alternatively, shallow aluminium trays may be filled with the gel and sealed with a plastic foil lid.

EXAMPLE 2

Dispersion Formulations

Following the procedure of Example 1, slow-release formulations of solid essential oils are prepared having the following composition of matter:

| Essential Oil | CARBOPOL ® EZ1 | Triethanolamine (50% solution) | Water |
|---|---|---|---|
| Thymol 25% | 0.38% | 0.76% | 73.86% |
| Thymol 20% | 0.38% | 0.76% | 78.86% |
| Thymol 15% | 0.48% | 0.96% | 83.56% |
| Thymol 10% | 0.48% | 0.96% | 88.56% |
| Thymol 30% | 0.38% | 0.76% | 68.86% |
| Thymol 35% | 0.38% | 0.76% | 63.86% |
| Thymol 40% | 0.38% | 0.76% | 58.86% |
| Camphor 25% | 0.38% | 0.76% | 73.86% |
| Calcium oxalate to 25% | 0.38% | 0.76% | 73.86% |

EXAMPLE 3

Suspension Formulations 0.38 parts of CARBOPOL® EZ1 are slowly added to 73.86 parts of water with stirring. 25 parts of cineol (eucalyptol) are suspended using a high speed stirreer until a homogeneous suspension is achieved. To the obtained suspension, 0.76 parts of a 50% aqueous solution of triethanolamine is added for cross-linking purposes, forming a gel.

The gel mixture is divided into 50 g portions and placed on shallow plastic tray dispensers. The surface of the tray is hermetically sealed with an aluminium or plastic foil lid. Alternatively, shallow aluminium trays may be filled with the gel and sealed with a plastic foil lid.

In a similar manner, the following formulations of liquid essential oils are prepared:

| Essential oil | CARBOPOL ® EZ1 | Triethanolamine (50% solution) | Water |
|---|---|---|---|
| Cineol 25% | 0.38% | 0.76% | 73.86% |
| Limonene 25% | 0.38% | 0.76% | 73.86% |
| Menthol 25%* | 0.38% | 0.76% | 73.86% |
| Neem-oil 25% | 0.38% | 0.76% | 73.86% |
| Acetic acid 30% | 0.48% | 0.96% | 68.56% |
| Formic acid 25% | 0.48% | 0.96% | 73.56% |

*process run at 40° C.

EXAMPLE 4

Biological Test

Two trays of the 25% thymol matrix slow-release formulation obtained from the preparation of Example 1, containing 50 grams of the slow-release gel each, are opened by removing the foil sealing lid and placed in a beehive on top of the broad frames. The test is started by placing the trays in the beehives, and is continued for 6 weeks. The average temperature inside and outside the beehives is recorded. The average temperature inside the beehive was 33 to 34° C., while outside the temperature varied between 17 and 35° C. (night/day).

After 4 to 6 weeks, the infestation of the bee colony is assessed in comparison to an untreated control beehive by counting the total number of mites killed during the treatment and divided by the same total plus the number of mites falling after a final treatment with an acaricide, killing all surviving mites.

The results are as follows:

| Treatment | Infestation at start | Infestation after 4 weeks | Reduction of Infestation in % |
|---|---|---|---|
| Thymol | | | |
| 1 tray per hive | 3240 | 1675 | 48.3% |
| 2 trays per hive | 2446 | 557 | 77.2% |
| Control | 2873 | 2502 | 12.9% |

CONCLUSION

The slow release formulation tested above is effective against *Varroa jacobsoni* infestations of bee hives as compared to control (non-treated) colonies.

What is claimed is:

1. A slow-release gel formulation for the control of acarid, lepidopteran, fungal and bacterial pest infestations in colonies of honeybees, comprising at least 15% by weight of thymol.

2. A formulation according to claim 1, wherein the thymol is delivered at an effective dose over a period of at least one reproductive cycle of the pest.

3. A formulation according to claim 1, wherein the gel is in the form of gel strips, gel pellets, gel tablets, or a dispenser tray filled with said gel strips, gel pellets or gel tablets, or the gel is within a shallow tray dispenser with a hermetically sealing lid.

4. A slow release gel formulation according to claim 1, wherein the gel formulation comprises at least 25% by weight thymol.

* * * * *